US00PP21605P2

(12) United States Plant Patent
Bédard

(10) Patent No.: US PP21,605 P2
(45) Date of Patent: Jan. 4, 2011

(54) FLORIBUNDA ROSE PLANT NAMED 'WEKMONGROS'

(50) Latin Name: *Rosa hybrida*
Varietal Denomination: WEKmongros

(75) Inventor: Christian Bédard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/589,830

(22) Filed: Oct. 29, 2009

(51) Int. Cl.
*A01H 5/00* (2006.01)

(52) U.S. Cl. ..... Plt./146
(58) Field of Classification Search ..... Plt./146
See application file for complete search history.

(56) References Cited

U.S. PATENT DOCUMENTS

PP17,822 P3 6/2007 Sproul

*Primary Examiner*—Kent L Bell
(74) *Attorney, Agent, or Firm*—McKees, Voorhees & Sease, P.L.C.

(57) ABSTRACT

A new variety of Floribunda rose suitable for garden decoration, having flowers of caramel orange coloration.

1 Drawing Sheet

Classification: The present invention relates to a new *Rosa hybrida* plant.

Variety denomination: The new plant has the varietal denomination 'WEKmongros'.

BACKGROUND OF THE INVENTION

This invention relates to a new and distinct variety of Floribunda Rose. It has as its seed parent the variety known as 'KORfalt' (not patented) and as its pollen parent the variety known as 'WEKsproulses' (U.S. Plant Pat. No. 17,822).

SUMMARY OF THE INVENTION

Among the features which distinguish the new variety from other presently available and commercial rose cultivars known to the inventor are the following combinations of characteristics: its unique caramel orange flower coloration, its many stamens, its dark glossy foliage and its heavy red suffusion on the rachis and petiole on the young leaf. The plant has an upright somewhat rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKmongros' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'KORfalt' by the following combination of characteristics: whereas 'WEKmongros' bears flowers of caramel orange coloration with double petalage (about 15 to 23 petals), 'KORfalt' bears flowers of deep yellow coloration with significantly heavier petalage (about 25 to 30 petals).

The new variety may be distinguished from its pollen parent, 'WEKsproulses' by the following combination of characteristics: whereas 'WEKmongros' bears medium sized flowers (about 7.9 to about 11.2 cm. in diameter) of caramel orange coloration, 'WEKsproulses' bears significantly larger flowers (about 9.4 to about 14.3 cm. in diameter) of warm golden brown coloration. The new variety is classified as a floribunda rose with an upright somewhat rounded medium height growing habit (about 80 to about 100 cm. in height), whereas the pollen parent is classified as a grandiflora rose with an upright and rounded moderately spreading medium height significantly taller growing habit (about 100 to about 130 cm. in height).

COMPARISON WITH THE CLOSEST COMMERCIALLY AVAILABLE CULTIVAR

The new variety may be distinguished from its closest commercially available cultivar, 'AROsnap' by the following combination of characteristics: whereas 'WEKmongros' bears flowers of caramel orange coloration with double petalage (about 15 to 23 petals), 'AROsnap' bears flowers of a unique shade of orange coloration with significantly heavier petalage (about 25 to 36 petals). The new variety has an upright somewhat rounded medium height growing habit (about 80 to about 100 cm. in height), whereas the closest commercially available cultivar has a significantly shorter growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong short to medium stems (about 13 to about 38 cm.). Outdoors, the plant blooms abundantly and nearly continuously during the growing season. The flowers have a slight tea fragrance.

BUD

The peduncle is about 2.3 to about 4.4 cm. in length, of average caliper (about 0.2 to about 0.3 cm. in diameter), and usually erect. It is moderately rough, with many stipitate glands, and few hairs. Peduncle color is between 146B and 146A sometimes moderately suffused, especially on the side exposed to the sun, with between 183B and 187A.

Before the calyx breaks, the bud is about 1.0 to about 1.8 cm. in diameter at the widest point, about 1.6 to about 2.1 cm. in length, and pointed in shape. The surface of the bud bears few foliaceous appendages, some stipitate glands and few hairs, usually with slender entire foliaceous parts extending beyond the tip of the bud about ½ or more of its length. Bud color is between 146B and 147B sometimes lightly suffused, especially on the side exposed to the sun, with between 183B and 187A.

The sepals are about 2.4 to about 3.7 cm. in length and about 0.7 to about 1.0 cm. in width at the widest point. The outer surface color of the sepal is between 146B and 147B sometimes lightly suffused, especially on the side exposed to the sun, with between 183B and 187A. The inner surface color of the sepal is near 138B broadly bordered by near 137A. After the sepals open, the inner surface color is often moderately suffused, especially on the area exposed to the sun, with between 187A and 187B. The inner surface of the sepal is covered with fine wooly tomentum; sepal margins are lined with some stipitate glands and hairs.

The receptacle of the flower is of medium length (about 0.5 to about 0.8 cm.) and somewhat heavy in caliper (about 0.7 to about 1.0 cm. in diameter). The receptacle is cup-shaped in form. Its surface is very smooth with some hairs and with thick fleshy walls. The receptacle color is between 144A and 147B.

As the petals open (after the calyx breaks), the bud is about 1.7 to about 2.3 cm. in diameter at the widest point, about 1.9 to about 3.0 cm. in length, and moderately ovoid to somewhat pointed in form. The color of the under surfaces of the newly opened petals is between 47A and 42B. At the point where the petal attaches, there is a large zone of between 13B and 12A. The color of the upper surfaces of the newly opened petals is between 26A and 168C usually heavily suffused with between 46A and 53A. At the point where the petal attaches, there is a moderately large zone of between 12A and 13A.

BLOOM

When fully open, the bloom ranges from about 7.9 to about 11.2 cm. in diameter. Petalage is double with about 15 to 23 petals and about 4 to 14 petaloids irregularly arranged. When partially open, the bloom form is moderately high centered to somewhat cupped, and the petals are loosely spiraled to somewhat cupped with petal edges moderately reflexed outward. When fully open, the bloom form is cupped, and the petals are loosely cupped with petal edges very reflexed outward to somewhat rolled.

PETALS

The substance of the petals is moderately heavy and of medium to somewhat thick thickness, with upper surfaces moderately satiny and under surfaces slightly shiny to matte. The petals are about 3.6 to about 4.5 cm. in length and about 2.5 to about 4.4 cm. in width at the widest point. Petal margins are entire.

The outer petals are nearly round to somewhat obovate in shape with rounded apices.

The inner petals are moderately obovate to somewhat oblanceolate in shape with rounded apices.

Petaloids are about 1.1 to about 3.4 cm. in length and about 0.3 to about 1.3 cm. in width at the widest point. Petaloids are irregularly shaped somewhat oblanceolate to subulate with rounded apices.

NEWLY OPENED FLOWER

The under surface color of the outer, intermediate and inner petals is between 31C and 168C usually moderately suffused with between 53C and 53D. At the point where the petal attaches, there is a large zone of between 13C and 14C. The upper surface color of the outer, intermediate and inner petals is between 26B and 168C usually moderately suffused with between 53B and 53C. At the point where the petal attaches, there is a moderately large zone of between 13A and 13B.

The under and upper surface colors of the petaloids are similar in coloration to the upper and under surfaces of the intermediate and inner petals.

The general tonality of the newly opened flower is between 26B and 168C usually moderately suffused with between 53B and 53C.

THREE-DAY-OLD FLOWER

The under surface color of the outer, intermediate and inner petals is between 54C and 27C. At the point where the petal attaches, there is a large zone of between 8C and 5D. The upper surface color of the outer, intermediate and inner petals is between 54C and 27C. At the point where the petal attaches, there is a moderately large zone of between 6D and 10B.

The under and upper surface colors of the petaloids are similar in coloration to the upper and under surfaces of the intermediate and inner petals.

The general tonality of the three-day-old flower is between 54C and 27C.

On the spent bloom, the petals usually persist, fading to between 155A and 155B usually lightly suffused with near 60D.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 155) and are arranged regularly about the pistils; a few are mixed with petaloids. The filaments are of variable length (about 0.4 to about 1.1 cm.) most with anthers. Filaments are between 14A and 15A in color. The anthers are moderately small for the class and all open approximately at the same time. Anther color when immature is near 21A on the external part and near 11C on the internal part. Anther color at maturity is near 164A on the external part and near 200A on the internal part. Pollen is very abundant and near 16C in color.

FEMALE REPRODUCTIVE ORGANS

Pistils vary in number (average about 75). The styles are moderately even, average in length (about 0.4 to about 0.9 cm.), somewhat thin in caliper, and loosely separated to somewhat bunched. Stigma color is between 9C and 8B. Style color is between 154C and 1C often moderately suffused with near 53B. Ovaries are usually all enclosed in the calyx.

Hips are of average length (about 1.8 to about 2.4 cm.), nearly rounded in form, and between 28A and 30B in color when ripe. The hip surface is very smooth with thick fleshy walls. The sepals are moderately permanent, and usually straight in shape.

The seeds are irregularly rounded, smooth in texture, approximately 16 to about 27 per hip, about 0.4 to about 0.6 cm. in diameter at the widest point and between 161B and 163D in color.

FOLIAGE

The compound leaves are usually comprised of three to seven leaflets and are borne abundantly. The five-leaflet leaves are about 8.8 to about 12.9 cm. in length and about 7.3 to about 10.6 cm. in width at the widest point, moderately leathery to somewhat crisp in texture, and glossy in finish on the upper side and matte in finish in the under side. The terminal leaflets are about 4.9 to about 6.5 cm. in length and about 2.5 to about 3.6 cm. in width at the widest point, shaped moderately ovate to somewhat oval with acuminate apices and rounded to somewhat acute bases. Their margins are usually simply serrate.

The upper surface color of the mature leaf is between 139A and 147A. The under surface color of the mature leaf is between 147B and 148C. The upper surface color of the young leaf is between 147A and 146A, often moderately suffused especially toward the edge of the leaflet with between 187A and 183A. The under surface color of the young leaf is between 139C and 148C, often heavily suffused with between 187B and 183A.

The rachis is somewhat light in caliper and moderately rough. The upper side is shallowly grooved with some stipitate glands on the edges of the grooves. The under side of the rachis is moderately rough with few stipitate glands and small prickles. The rachis color is near 146D on the under side and near 146B on the upper side often heavily suffused on the young leaf with between 187B and 183A.

The stipules are about 0.8 to about 1.1 cm. in length and of moderately narrow width (about 0.3 to about 0.5 cm.) with medium length straight points that usually turn out at an angle of more than 45 degrees. The stipule color is between 137B and 137C.

The petiole is somewhat light in caliper and moderately rough. The upper side is shallowly grooved with some stipitate glands on the edges of the grooves. The under side of the petiole is moderately rough with few stipitate glands and small prickles. The petiole is about 0.6 to about 1.2 cm. in length and about 0.1 to about 0.15 cm in diameter at the widest point. The petiole color is near 146D on the under side and near 146B on the upper side often heavily suffused on the young leaf with between 187B and 183A.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright somewhat rounded medium height growing habit (about 80 to about 100 cm. in height and about 50 to about 65 cm. spread at the widest point), with full branching. It displays vigorous growth and the canes are of medium caliper for the class (about 1.2 to about 1.8 cm. in width at the widest point).

The color of the major stems is between 146B and 146C. They bear some large prickles that are about 1.0 to about 1.4 cm. in length. The large prickles are angled slightly downward with a medium length broad oval base; prickle color is between 164A and 166C. The major stem bears few small prickles of similar shape and coloration.

The color of the branches is between 146B and 148B. They bear few large prickles which are of similar shape to the large prickles on the major stems. Prickles are about 0.6 to about 0.9 cm. in length. The color is between 152D and 153A sometimes lightly suffused with near 187D. The branches bear few small prickles of similar shape and coloration.

The color of the new shoots is between 146C and 148B often moderately suffused with between 183A and 187A. They bear few large prickles which are of similar size and shape to the large prickles on the branches; prickle color is between 152D and 153A often heavily suffused with between 187C and 187D. The shoots bear few small prickles of similar shape and coloration.

I claim:

1. A new and distinct Floribunda rose plant of the variety substantially as described and illustrated herein.

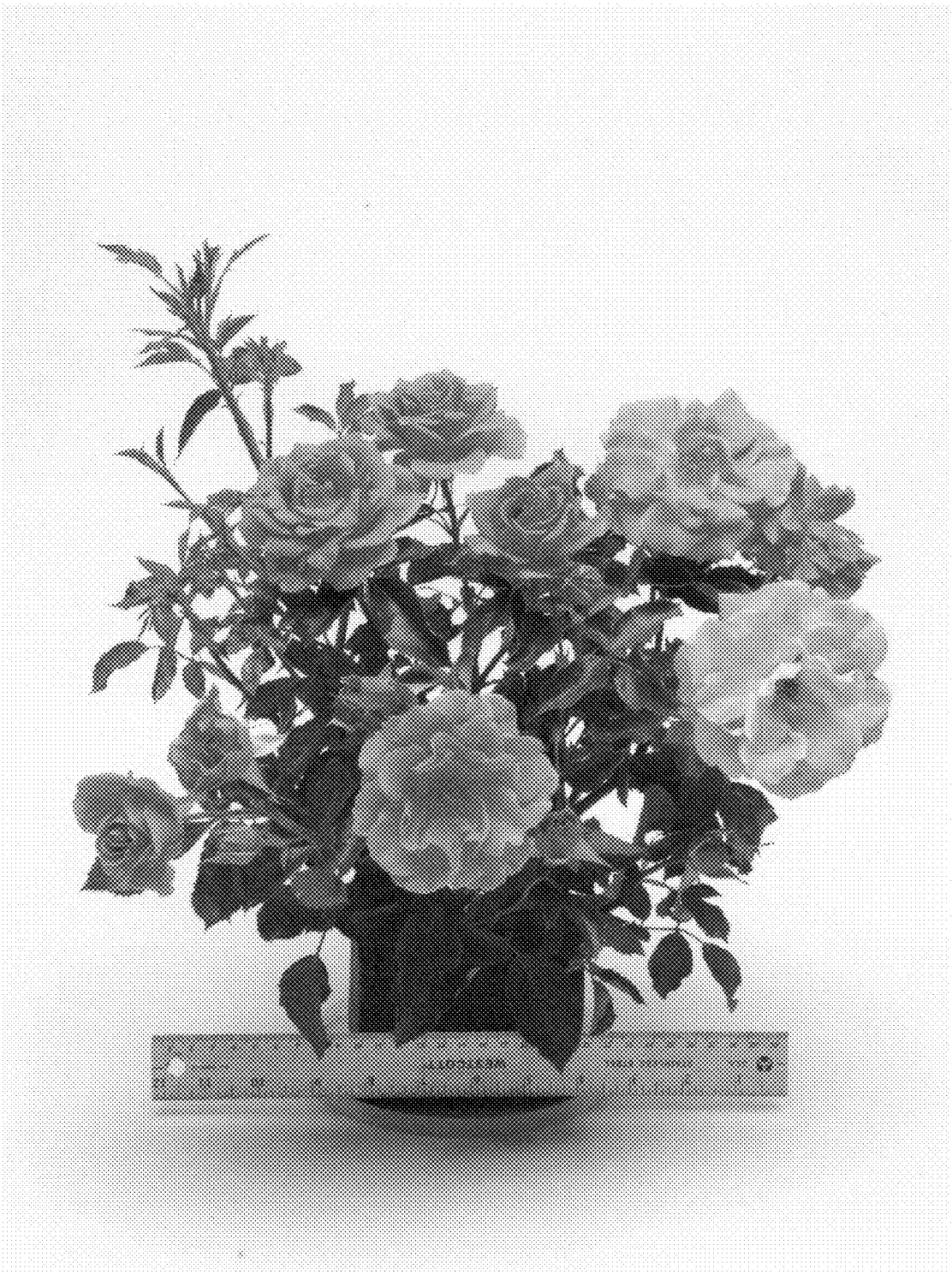

* * * * *